(12) United States Patent
Gilligan et al.

(10) Patent No.: US 7,730,904 B2
(45) Date of Patent: Jun. 8, 2010

(54) MODULAR MICROFLUIDIC SYSTEM

(75) Inventors: Mark Peter Timothy Gilligan, Royston (GB); Philip James Homewood, Walthamstow (GB); Robert J. Ranford, Stortford (GB); Paul M. Crisp, Elsworth (GB)

(73) Assignee: Syrris Limited (GB)

( * ) Notice: Subject to any disclaimer, the term of this patent is extended or adjusted under 35 U.S.C. 154(b) by 1162 days.

(21) Appl. No.: 11/304,188

(22) Filed: Dec. 15, 2005

(65) Prior Publication Data

US 2006/0150385 A1 Jul. 13, 2006

(30) Foreign Application Priority Data

Dec. 15, 2004 (GB) .................................. 0427464.3

(51) Int. Cl.
*F03B 11/02* (2006.01)
(52) U.S. Cl. .................................... 137/561 R; 137/833
(58) Field of Classification Search .................. 137/266, 137/263, 833, 561 A, 561 R
See application file for complete search history.

(56) References Cited

U.S. PATENT DOCUMENTS

| 5,580,523 | A | 12/1996 | Bard | 422/50 |
|---|---|---|---|---|
| 5,738,728 | A | 4/1998 | Tisone | 118/638 |
| 5,738,783 | A | 4/1998 | Shrota et al. | 210/198.2 |
| 5,743,960 | A | 4/1998 | Tisone | 118/683 |
| 6,027,479 | A | 2/2000 | Alei et al. | 604/131 |
| 6,488,895 | B1 | 12/2002 | Kennedy | 422/100 |
| RE38,281 | E | 10/2003 | Tisone | 422/100 |
| 2002/0119078 | A1* | 8/2002 | Jansa et al. | 422/103 |
| 2003/0156995 | A1 | 8/2003 | Gilligan et al. | 422/100 |

FOREIGN PATENT DOCUMENTS

WO   WO 02/030560 A2   4/2002

\* cited by examiner

*Primary Examiner*—John Rivell
*Assistant Examiner*—Craig M Schneider
(74) *Attorney, Agent, or Firm*—Ballard Spahr LLP

(57) ABSTRACT

An apparatus (10) for performing microfluidic processes comprising a base (50), a plurality of fluidic modules (20) releasably attached to the base (50), each fluidic module (20) comprising a fluid port (25) and a microfluidic manifold module (40) comprising a plurality of ports (45). A frame (70) is attached to the base (50) for releasably retaining the microfluidic manifold module (40), the frame (70) being moveable relatively to the base (50) to move the microfluidic manifold module (40) into contact with the fluidic modules (20) such that each fluid port (25) of the fluidic modules (20) aligns and seals with a respective port (45) on the microfluidic manifold module (40) thus completing a microfluidic circuit. A method for constructing and testing the apparatus (10) is also disclosed.

14 Claims, 6 Drawing Sheets

MODULAR MICROFLUIDIC SYSTEM

CROSS REFERENCE TO RELATED APPLICATIONS

The present application claims priority to Great Britain Application No. 0427464.3, filed Dec. 15, 2004, which application is incorporated herein fully by this reference.

BACKGROUND OF THE INVENTION

Field of the Invention

The present invention relates to a modular apparatus for performing microfluidic processes.

The concept of integrating a series of processes onto a single microfluidic device or chip has been well documented. Processes typically include pumping, mixing, heating, sensing and separating. Such systems are known as 'Lab-on-a-chip' (LOC) systems and also cover 'Micro Total Analysis Systems' (μTAS). In such systems a chemical reagent, biological sample or a cell goes through a series of processes on a chip. The aim might be to analyse a sample/cell or to synthesise a new compound.

Miniaturisation of laboratory processes is considered to be of key importance in the future of biological and chemistry science. Chemical and biological reactions happen faster at micro scale as a result of lower diffusion distances and efficient heat transfer. Less material is used in reactions resulting in cheaper and more environmentally friendly operation.

Microfluidic devices have other potential benefits above conventional systems including simple integration of devices, access to information about reaction kinetics and easy scale up.

A microfluidic chip is well known in the art and is typically a planar layered device fabricated using processes pioneered in the microelectronics industry. This normally involves using substrate materials such as silicon or glass wafers and processes such as photolithography, etching, metal deposition and anodic/thermal bonding. Microfabrication techniques have evolved so that devices can also be manufactured from polymer layers, using hot embossing techniques to create features and welding or adhesives to create bonds between layers.

The term "microfluidic device", is believed to be a term which is clearly understood in the art. The term is best understood functionally as relating to a device which is sufficiently small that diffusional mixing predominates and efficient heat transfer occurs, resulting in optimal reaction conditions in the microchannel. The dimensions of the microchannel should be sufficiently small that the flow results in a low Reynold's number ($<10^3$) and a predominantly laminar flow regime.

Generally at its narrowest point, the microchannel should have, in cross-section, a maximum internal dimension of 5-1000 μm, and preferably 5-500 μm. However, it is possible to envisage a channel which has a long thin cross-section having a dimension greater than 1000 μm, but which still operates as a microchannel as it is small in other dimensions.

Therefore, it might be more appropriate to define a microfluidic device as having a channel with a cross-section in a plane perpendicular to the direction of flow which, at its narrowest part, is sized so that the largest circle which can be drawn in the cross-section has a diameter of <1000 μm (and preferably <500 μm). In other words, if the cross-section is such that a circle of >1000 μm can be drawn within the cross-section, it will not operate as a microchannel.

With an increasing range of fabrication techniques and also increasing on-chip functions, it is often the case that a single microfluidic chip with a single fabrication process, cannot deliver the functionality required for a whole system. The concept of having a microfluidic system that integrates multiple microfluidic chips has therefore become popular.

There are also several cost benefits of going to a "multiple chip" system. The cost of integrating all the required functions onto a single chip can be very high as the fabrication process required to do this will be very complex. By using multiple chips the lowest cost fabrication process can be chosen for each chip, reducing the overall system cost. The second benefit is related to chip failure either during fabrication or during operation. If all the functions are integrated onto one chip then the whole device needs to be replaced if one thing fails. If multiple chips are used then typically only one chip needs to be replaced. The cost of a failure is therefore reduced significantly.

A number of modular systems which integrate multiple microfluidic chips are known in the art. Examples of such modular systems are given in WO 2004/022233, WO 0230560, U.S. Pat. No. 5,580,523 and U.S. Pat. No. 6,488,895. In these systems, the microfluidic chips are integrated by fixing the individual chip modules to one another, or to a manifold. Generally, fasteners such as screws, pins or clips are used to hold the individual modules together. The fluidic paths between the microfluidic chips are generally sealed by means of o-rings or other similar sealing devices.

One of the problems with the known modular systems is ensuring that the fluidic paths between the modules are sealed correctly. Poor sealing of the fluidic paths can arise if the sealing members do not receive sufficient compressive force to completely seal the fluidic path. This can be due to the fasteners being incorrectly installed, incompletely engaged or missing. In addition, it is often not possible to determine whether the fluidic paths have been sealed correctly before the microfluidic system is put into operation.

If one or more of the fluidic paths are incorrectly sealed the system will not function properly. Incorrect sealing may lead to expensive or dangerous chemical reagents being lost and valuable lab time being wasted. Additionally, if a fluidic path is inactive due to incorrect sealing, a reaction or experiment may be run to completion without the fault being detected.

SUMMARY OF THE INVENTION

The present invention provides an apparatus for performing microfluidic processes comprising, a base, a plurality of fluidic modules releasably attached to the base, each fluidic module comprising a fluid port, a microfluidic manifold module comprising a plurality of ports, a frame attached to the base for releasably retaining the microfluidic manifold module, the frame being moveable relatively to the base to move the microfluidic manifold module into contact with the fluidic modules such that each fluid port of the fluidic modules aligns and seals with a respective port on the microfluidic manifold module thus completing a microfluidic circuit.

Engaging the individual modules by means of relative motion between the base and the frame has a number of benefits. The sealing of the fluidic paths between the individual modules can be controlled by controlling the movement of the frame. Sufficient motive force can be applied to the frame to ensure complete sealing of the fluidic paths, and the speed of approach can be optimised to further ensure correct sealing of the fluidic paths. The apparatus of the present invention has the further advantage that the location and fixing of the individual modules is divorced from the sealing of the fluidic paths. This reduces greatly the possibility of damage to the seals as the apparatus is assembled.

In a preferred example the ports of the microfluidic manifold module comprise a plurality of inlet ports and at least one outlet port. However, in an alternative example the ports of the microfluidic manifold module may comprise a plurality of outlet ports and at least one inlet port.

The frame preferably comprises a sensor to detect the presence of the microfluidic manifold module. This provides a safeguard against the apparatus being operated without the microfluidic manifold module in place.

The relative motion between the base and the frame may be any relative motion which allows the individual modules to be brought into fluidic communication with one another, for example the frame may be connected to the base by a hinged connector. In a preferred example, the relative motion between the base and the frame is linear. The use of linear motion has the advantage that a uniform sealing force may be applied.

The fluidic modules which are releasably attached to the base may in certain circumstances be non-microfluidic, for example, a non-microfluidic pump module may be used. However, in a preferred example all of the fluidic modules are microfluidic.

Preferably, each fluidic module, and the microfluidic manifold module, have a housing surrounding an inner body to provide a support and location structure.

Each interface between a fluid port of the fluidic module and the corresponding inlet port of the microfluidic manifold module is preferably sealed by means of a resiliently deformable sealing member. In a preferred example the sealing member is an o-ring. More preferably, the sealing member is an o-ring of generally annular shape with flat ends.

In a further preferred example, each sealing member is retained in a recess formed in the housing of a fluidic module. Alternatively or additionally, the sealing member may be retained in a recess formed in the housing of the microfluidic manifold module.

The sealing members may be compressed by the force exerted upon them by the relative movement between the frame and the base, thus improving the integrity of the seals. The compression of the sealing members has the further advantage that any seal tolerances may be taken up. For example, if a batch of sealing members are at the lower end of their manufacturing tolerance, sufficient compressive force may be applied to ensure that the sealing members are compressed sufficiently to seal the fluidic paths.

In a preferred example the frame is arranged to stop moving relatively to the base when a predetermined reaction force is reached. This is advantageous since the elasticity of the seals may vary over time as a result of exposure to heat and solvents.

In an alternative preferred example, the frame is arranged to stop moving when a predetermined position is reached.

In a second aspect, the present invention provides a method for constructing and testing a modular apparatus for carrying out microfluidic processes, the method comprising, assembling a plurality of fluidic modules and a microfluidic manifold module to complete a microfluidic circuit, and testing the integrity of the microfluidic circuit by supplying pressurised gas to the circuit, sealing the circuit and measuring the gas pressure within the circuit after a predetermined time.

This second aspect of the present invention provides the advantage that it is possible to determine whether interfaces between the individual modules have been sealed correctly before the apparatus is operated.

In a preferred example the apparatus for carrying out microfluidic processes is assembled by releasably attaching a plurality of fluidic modules to a base, releasably attaching a microfluidic manifold module to a frame attached to the base, moving the frame relatively to the base such that ports in the fluidic modules align and seal with respective ports in the microfluidic manifold module such that the fluidic circuit is completed.

In a preferred example the gas is an inert gas. This has the advantage that the gas will not react with reagents contained within the microfluidic circuit.

The pressure within the microfluidic circuit may be measured by one or more pressure sensors located in the microfluidic circuit. A single sensor may be used to detect the pressure. This has the advantage of reducing the cost of the apparatus.

The pressure sensor may be located in one of the fluidic modules. In a preferred example, the or each pressure sensor is located in a fluidic pump module downstream of a pump. This has the advantage that the pressure of the fluid being pumped may be measured. Alternatively, the pressure sensor may be located in a gas supply line.

BRIEF DESCRIPTION OF THE DRAWINGS

Examples of the present invention will now be described with reference to the accompanying drawings, in which:

FIG. 1 depicts a modular microfluidic apparatus 10 comprising a base 50. Three pump modules 20a, 20b, 20c and a sensor module 30 are releasably attached to the base 50 as described below. A heater plate 80 is also fixed to the base 50. A reaction chip module 40 is also shown, the attachment of which will be described below.

DESCRIPTION OF THE PREFERRED EMBODIMENTS

Figure 1:
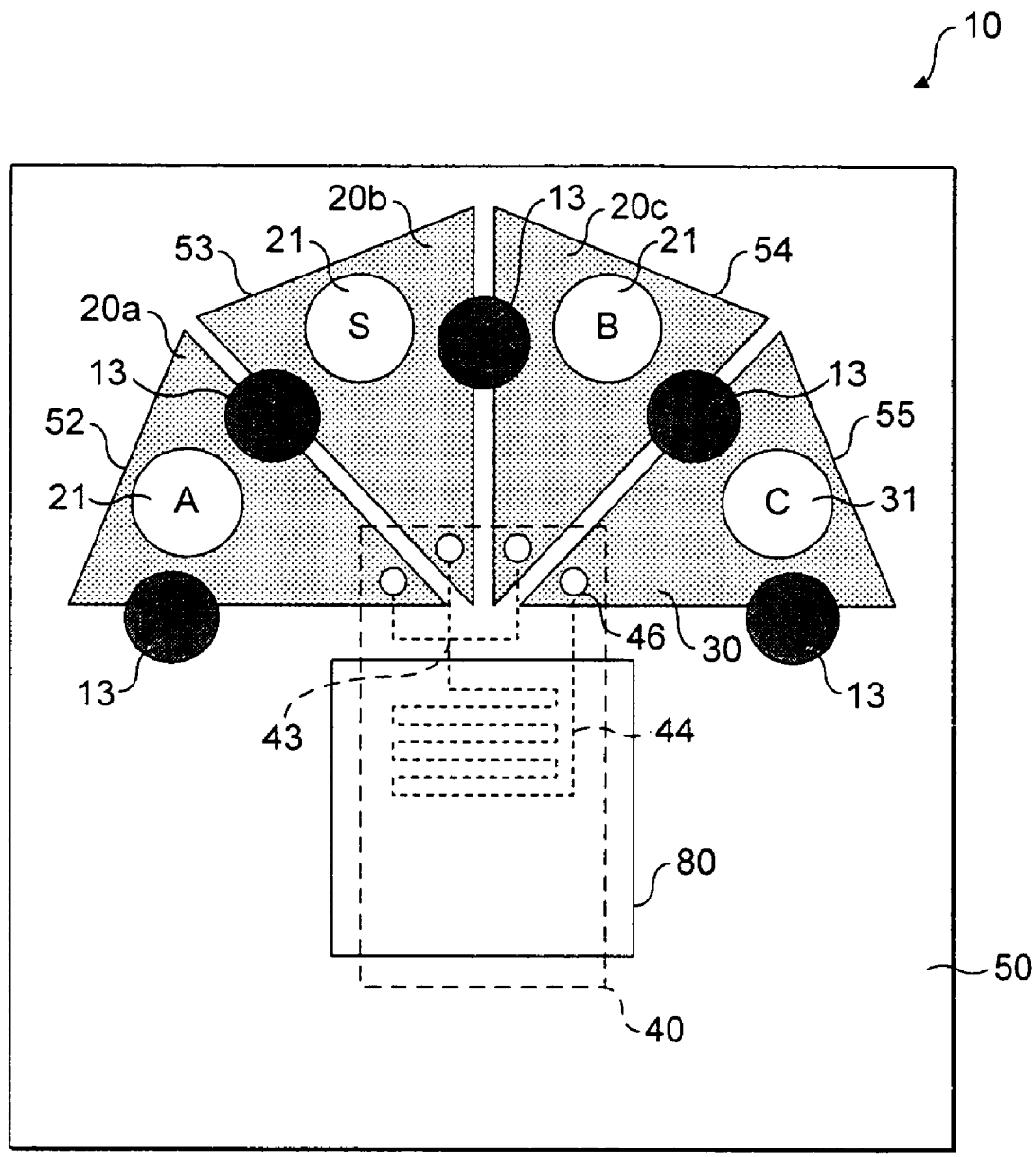
FIG. 1 is a schematic plan view of an apparatus according to the present invention that is used to carry out microreactions.
Figure 2:
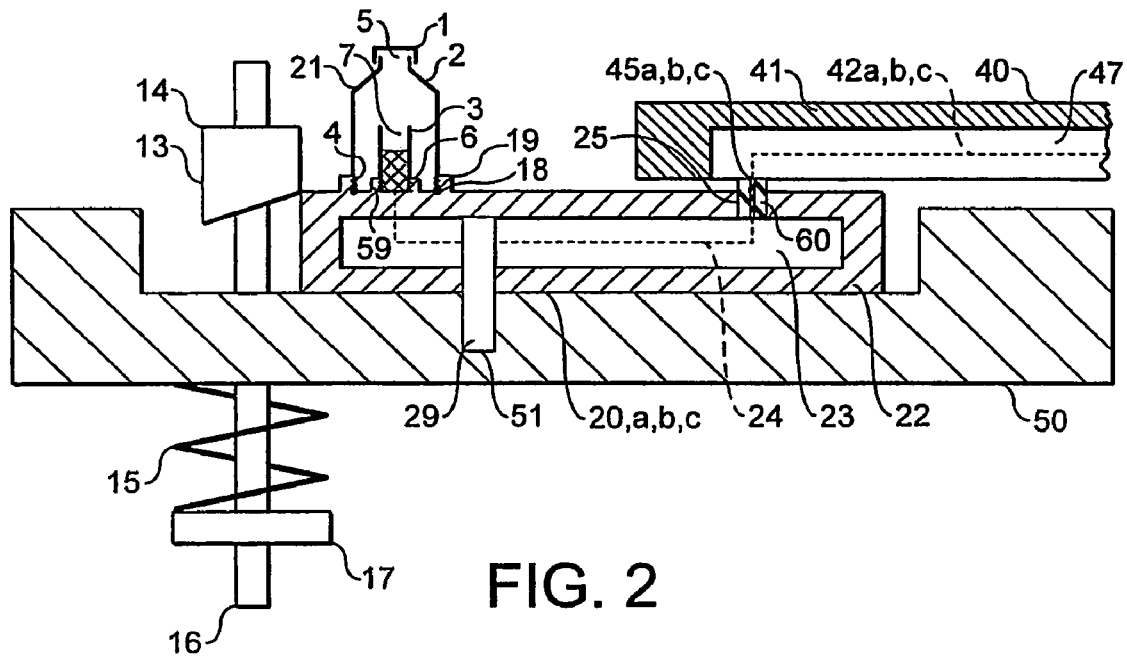
FIG. 2 is a partial schematic sectional side view of the apparatus of FIG. 1 depicting the fluidic connection between the pump modules and the reaction chip module.
Figure 9:
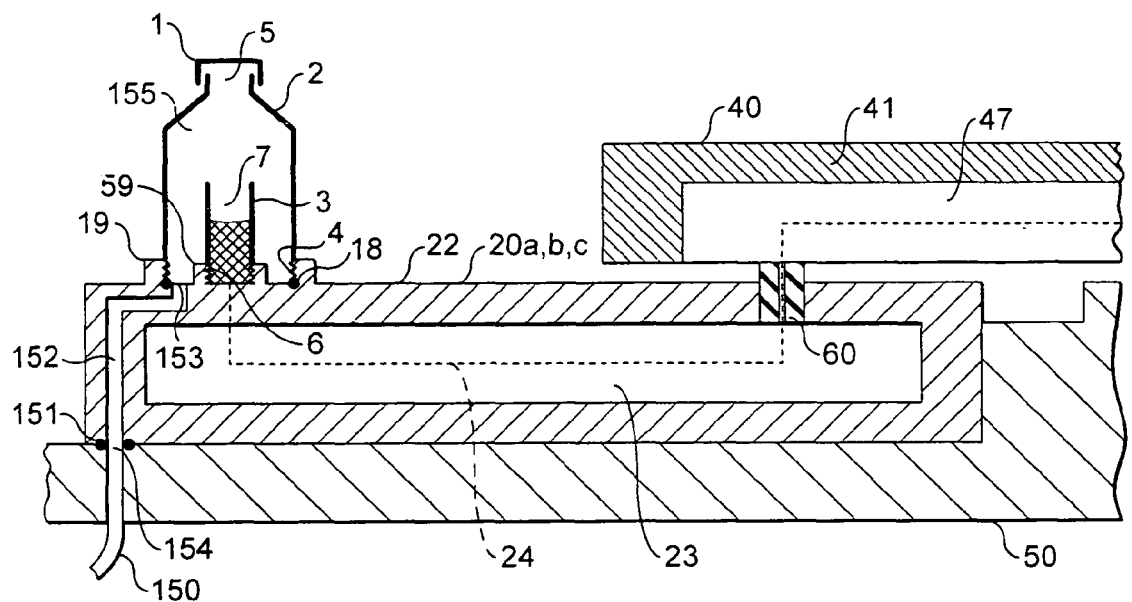
FIG. 9 is a partial schematic sectional side view of the apparatus of FIG. 1 depicting the connection of a gas supply.

Referring to FIGS. 1, 2 and 9, each pump module 20a, 20b. 20c comprises a reservoir 21 for supplying a reagent A or B, or a solvent S, to the reaction chip module 40. The reservoir 21 comprises an exterior portion 2 and an interior portion 3. The exterior portion 2 has an opening 5 at its upper end and a threaded section 4 at its lower end. The inner portion 3 has an opening 7 at its upper end and a threaded section 6 at its lower end. A rubber cap 1 closes the opening 5. The rubber cap 1 allows extra reagent to be added to the reservoir by syringe if required.

Each pump module 20*a*, 20*b*, 20*c* further comprises a housing 22 and a pump chip 23. The housing 22 has threaded sections 19 and 59 and a fluid port 25. An o-ring 18 is located within the threaded section 19. Two location pins 29 extend through the housing 22 and the chip 23 and protrude from the lower side of the pump module 20. The fluid port 25 has an o-ring 60 retained therein. The o-ring 60 has a substantially annular shape with flat ends.

The outer portion 2 and the inner portion 3 of the reservoir 21 are releasably attached to the housing 22 via the threaded sections 19 and 59. The o-ring 18 provides a gas tight seal between the interior of the reservoir 21 and the atmosphere.

Each pump chip 23 is of a planar layered construction. For example, a layered glass/polymer/glass construction. Each pump chip 23 comprises a microchannel 24 connecting the reservoir 21 to the fluid port 25 in the pump module housing.

Figure 3:
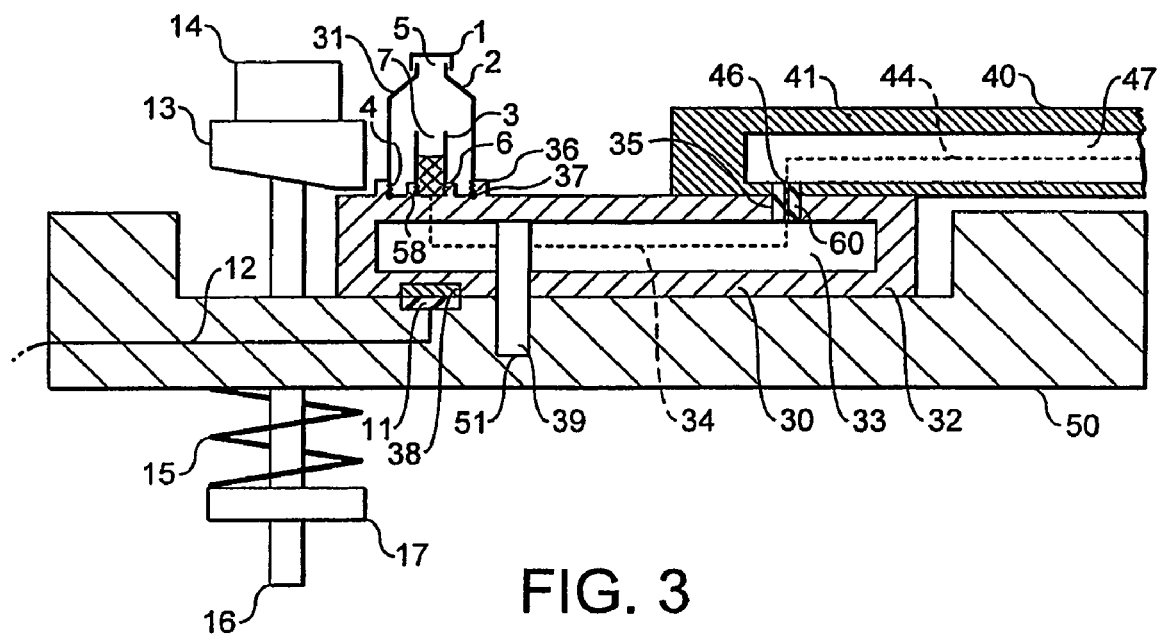
FIG. 3 is a partial schematic sectional side view of the apparatus of FIG. 1 depicting the fluidic connection between the sensor module and the reaction chip module.

Referring to FIGS. 1 and 3, the sensor module 30 has substantially the same construction as described above for the pump modules 20*a*, 20*b*, 20*c*. The sensor module 30 comprises a reagent reservoir 31 with the same construction as described above for the pump module reservoir 21.

The sensor module 30 further comprises a housing 32 and a sensor chip 33. The housing 32 has threaded sections 36 and 58 and a fluid port 35. An o-ring 37 is located within the threaded section 36. Two location pins 39 extend through the housing 32 and the chip 33 and protrude from the lower side of the sensor module 30. The port 35 has a sealing member 60 retained therein.

The outer portion 2 and the inner portion 3 of the reservoir 31 are releasably attached to the housing 32 via the threaded sections 36 and 58, the o-ring 37 provides a gas tight seal. The housing 32 of the sensor module further comprises an electrical connector 38 located on the lower surface of the sensor module 30.

The sensor chip 33 has a microchannel 34 which connects the port 35 to the reagent reservoir 31. The reaction sensor chip 33 is of a planar layered construction. For example, a layered glass/platinum/glass diffusion bonded construction. The electrical connector 38 is in electrical connection with the sensor chip 33.

Figure 4:
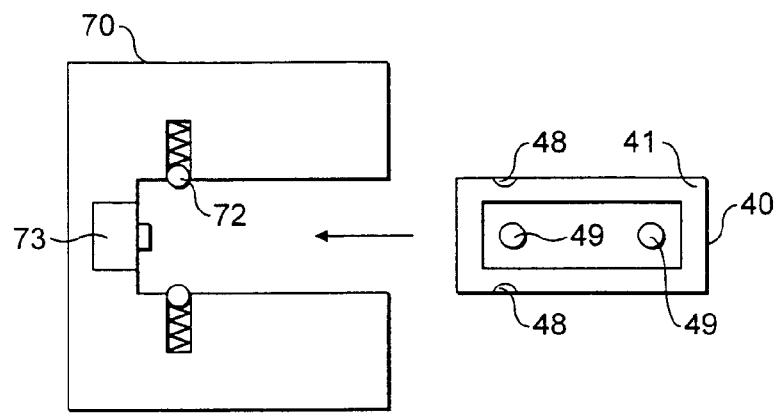
FIG. 4 is a schematic plan view of the frame for releasably retaining the reaction chip module.

Referring to FIGS. 1, 2, and 4, The reaction chip module 40 comprises a housing 41 and a reaction chip 47. The housing 41 has two semi-spherical indents 48 located on the outer surface. The reaction chip 47 comprises three inlet ports 45*a*, 45*b*, 45*c* and an outlet port 46. Three inlet microchannels 42*a*, 42*b*, 42*c* connect the inlet ports 45*a*, 45*b*, 45*c* to a reaction microchannel 44 via a microchannel junction 43. The reaction channel 44 connects the microchannel junction 43 to the outlet port 46. The reaction chip 47 is of a planar layer construction. For example, a layered glass/glass diffusion bonded construction. The reaction chip module 40 further comprises two location pins 49 which pass through the housing 41 and chip 47 and which protrude from the lower side of the reaction chip module 40.

The base 50 has eight receiving holes 51 for receiving the location pins 29 and 39 of the pump modules 20*a*, 20*b*, 20*c* and the sensor module 30 respectively. The base 50 further comprises five sprung latches 13 for holding the pump modules and the sensor module in place on the base 50. The spaces between the sprung latches 13 define four docking stations 52, 53, 54, 55 for the three pump modules 20*a*, 20*b*, 20*c* and sensor module 30 respectively. The sprung latches 13 comprise a knob 14 located at the upper end of a shaft 16, and a stopper plate 17 located at the lower end of the shaft 16. The shaft 16 passes through the base 50. A spring 15 is located between the stopper plate 17 and the base 50.

An electrical connector 11 is located on the upper surface of the base 50 at the docking station 55 of the sensor module 30. The electrical connector 11 has an electrical power supply 12.

Figure 5A:
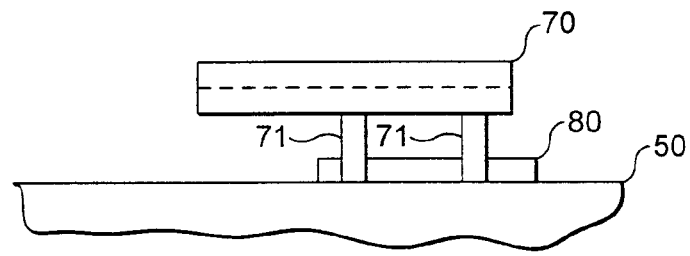
FIGS. 5a to 5c are a series of schematic side views of the apparatus of FIG. 1 depicting how the apparatus is assembled.
Figure 5B:
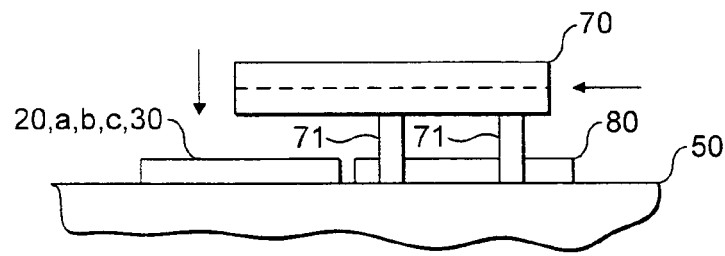
Figure 5C:
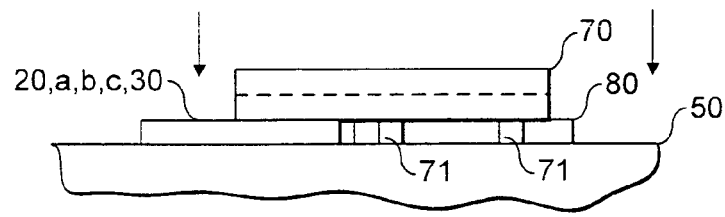

Referring to FIGS. 4 and 5*a*, the apparatus 10 further comprises a frame 70 moveably attached to the base 50. The frame 70 has four legs 71 retained within receiving holes in the base 50 (not shown). The legs 71 are constrained to move linearly by linear bearings located in the receiving holes. The frame 70 further comprises two ball spring plungers 72 and a microswitch 73. The microswitch 73 is connected to a system controller 110. FIGS. 5*a* to 5*c* depict how the microfluidic apparatus 10 is assembled. The pump modules 20*a*, 20*b*, 20*c* and the sensor module 30 are releasably attached to the base 50 by placing the location pins 29 and 39 in the receiving holes 51. The pump modules 20*a*, 20*b*, 20*c* and the sensor module 30 are then releasably secured by turning the knob 14 through 90° as illustrated in FIGS. 2 and 3.

Positioning and securing the sensor module 30 on the base 50 brings the base electrical connector 38 into contact with the sensor module electrical connector 11, thus providing an electrical supply to the sensor chip 33. In this example the sensor chip functions by measuring variations in electrical conductivity. However, any other type of sensor chip known in the art may be used.

The reaction chip module 40 is releasably attached to the frame 70 by sliding it into the frame via horizontal rails (not shown). The reaction chip module 40 is held in place by the ball spring plungers 72 which locate with the recesses 48 in the housing 41. The reaction chip module 40 takes its vertical alignment from the rails on the frame 70 and its horizontal alignment from the location pins 49 which locate with holes in the heater plate 80 and base 50 (not shown). Placement of the reaction chip module 40 in the frame 70 depresses the microswitch 73 thus indicating to the system controller 110 that the reaction chip module 40 is in place.

Once the pump modules 20*a*, 20*b*, 20*c*, the sensor module 30 and the reaction chip module 40 are in place, the frame 70 is lowered by a pneumatic drive to bring the reaction chip module 40 into contact with the pump modules 20*a*, 20*b*, 20*c*, the sensor module 30, and the heater plate 80. The frame 70 may be actuated by any driving means known in the art such as an electric motor or by mechanical levers.

When the reaction chip module 40 is in the lowered position, the reaction chip inlet ports 45*a*, 45*b*, 45*c* align with the pump module ports 25. Similarly, the reaction chip outlet port 46 aligns with the sensor module port 35. Thus, by lowering the reaction chip module 40 a microfluidic circuit is completed and a direct connection is made between the planar chip devices. The base 50 and frame 70 hold the pump modules, sensor module and reaction chip module in correct alignment so that the fluid ports align and the microfluidic circuit is completed. The reaction chip module 40 performs a function similar to a manifold in connecting all the microfluidic modules together.

The basic function of the apparatus 10 is to pump reagents A and B, and solvent S, from the reservoirs 21 to the microfluidic junction 43 where they mix and flow along a heated reaction channel 44. The reaction mixture then passes through a reaction sensor chip 33 before being collected in the reservoir 31.

Figure 6:
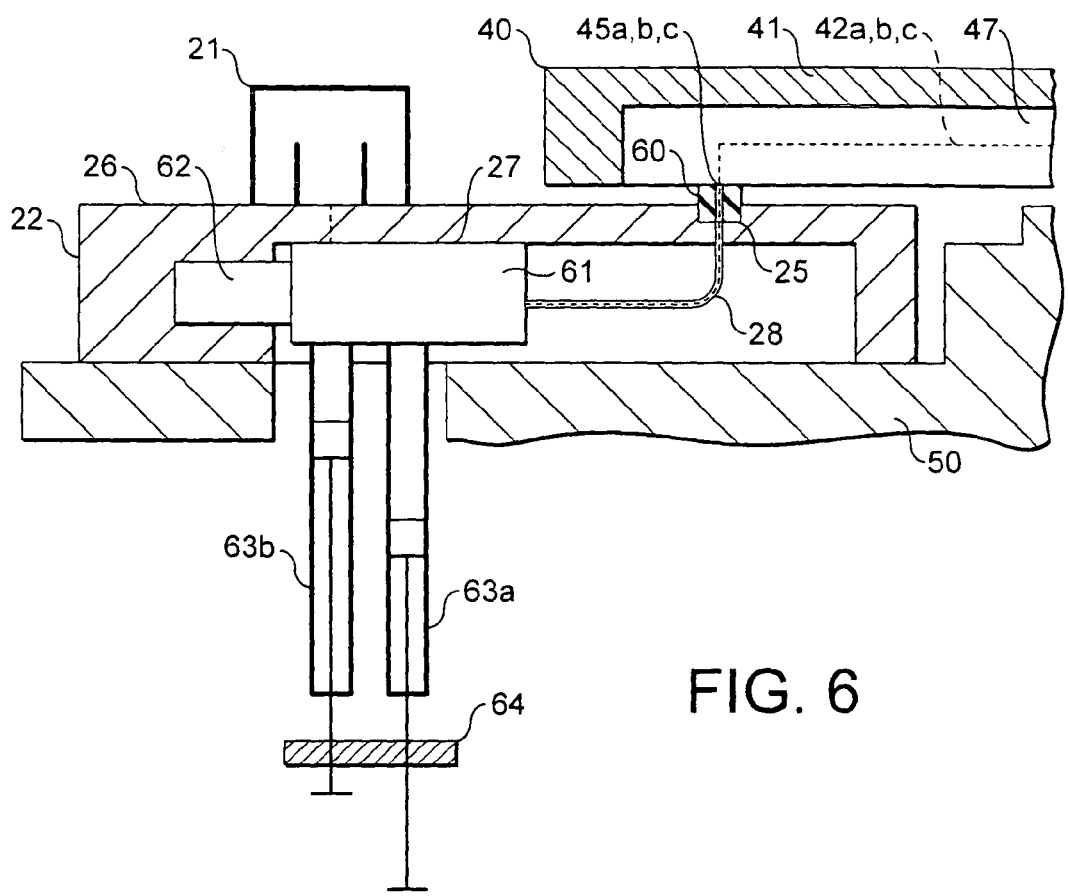
FIG. 6 is a partial schematic sectional side view of the apparatus of FIG. 1 depicting an alternative pump module to that shown in FIG. 2.

FIG. 6 shows a further embodiment of the present invention. For reasons of clarity, in cases where equivalent parts are shown the reference numerals used are the same as those given above. In this alternative embodiment, one or more pump modules 26 are used in place of one or all of the microfluidic pump modules 20a, 20b, 20c. The pump module 26 is not a microfluidic device, instead, a more conventional pump 27 is used as described below.

The pump 27 comprises a rotary valve 61 which is driven by a rotary drive 62. The pump 27 further comprises two glass syringes 63a, 63b which are driven by a linear drive 64. The rotary valve 61 and rotary drive 62 are located within housing 22 of the alternative pump module 26. The syringes 63a, 63b project from the lower side of the pump module 26 and into the base 50. The linear drive 64 is located in the base 50.

Figure 7:
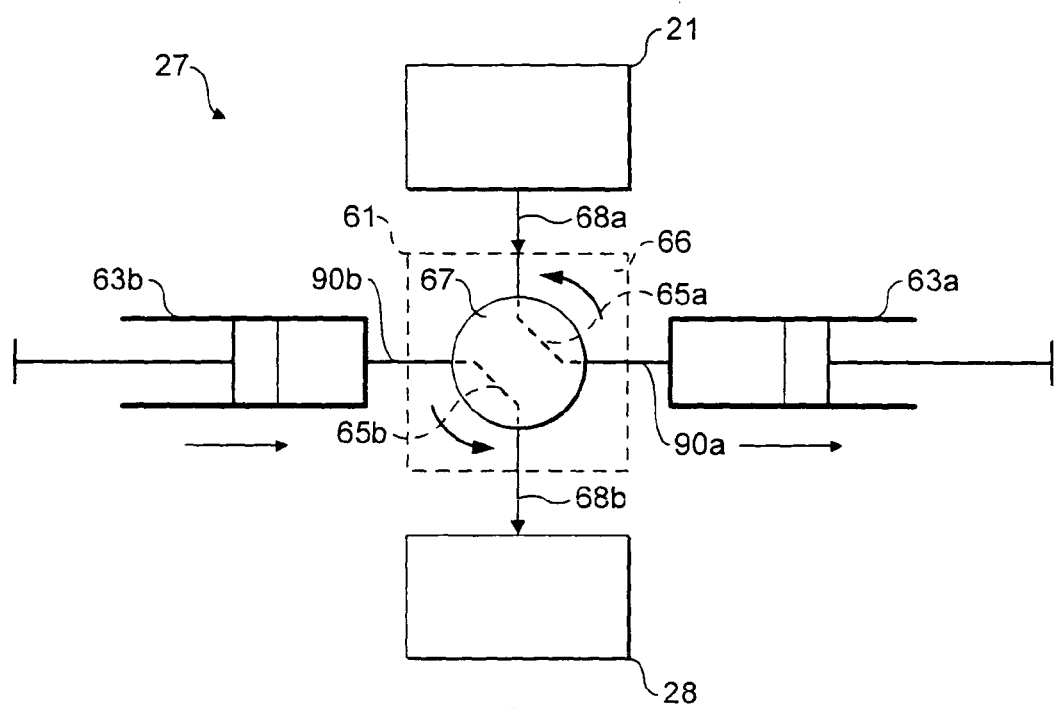
FIG. 7 is a schematic representation of the alternative pump of FIG. 6.

Referring to FIGS. 6 and 7, The rotary valve 61 comprises an outer body 66 and an inner body 67 which is able to rotate within the outer body 66. The inner body 67 comprises two discrete channels 65a, 65b. The outer body 66 comprises an inlet channel 68a and an outlet channel 68b. The outer body also comprises two syringe channels 90a, 90b.

The inlet channel 68a is connected to a fluid reservoir 21 located on the pump module 26 and the outlet channel 68b is connected to a polymer pipe 28 which leads to a port 25 in the housing 22 of the pump module 26. The syringe channels 90a, 90b are connected to the syringes 63a, 63b respectively.

FIG. 7 depicts the operation of the pump 27. In a first action, syringe 63a aspirates fluid from the reservoir 21 via the inlet channel 68a, the inner body channel 65a and the syringe channel 90a. At the same time, syringe 63b dispenses fluid into the polymer pipe 28 via the outlet channel 68b, the inner body channel 65b and the syringe channel 90b. The rotary drive 62 drives the rotary valve 61 into a second position such that inner channel 65a connects syringe channel 90b with outlet channel 68b, and inner channel 65b connects syringe channel 90a and inlet channel 68a. The process is then reversed such that syringe 63a dispenses its fluid contents to the polymer pipe 28 and syringe 63b aspirates fluid from the reservoir 21. The process repeats continuously to pump fluid from the reservoir 21 to the reaction chip module 40.

A sealing member 60 is used to make the fluid connection between the pump module 26 and the reaction chip module 40 as before. However, in this case the polymer pipe 28 is located inside the sealing member 60 to create a seal.

The method for constructing and testing a modular apparatus for carrying out microfluidic processes will now be described.

Figure 8:
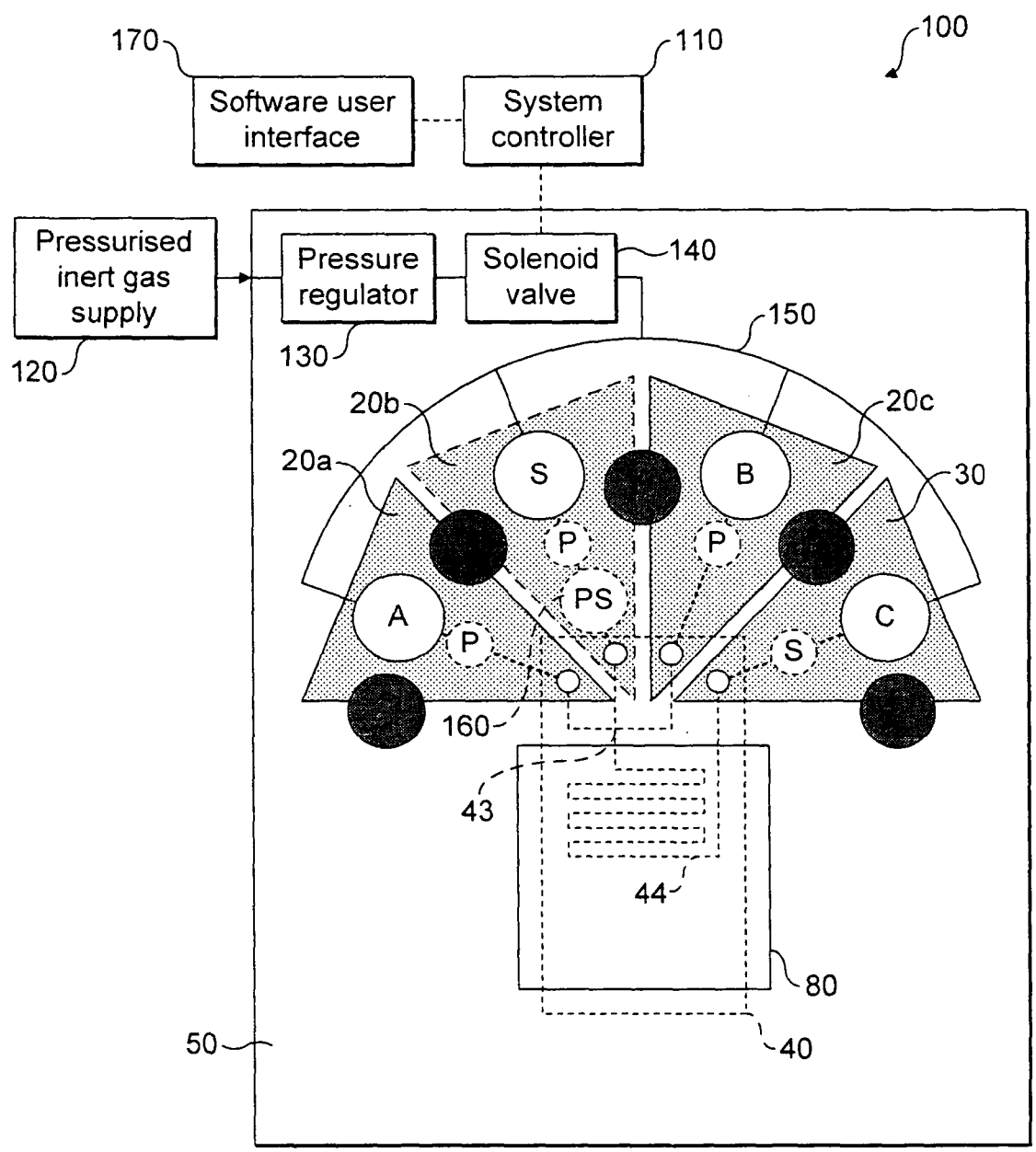
FIG. 8 is a schematic plan view of the apparatus of FIG. 1 further comprising a test apparatus to verify the integrity of the fluidic circuit.

Referring to FIG. 8, the apparatus of FIG. 1 is shown further comprising a system test apparatus 100. For reasons of clarity, in cases where equivalent parts are shown the reference numerals used are the same as those given above. The system test apparatus 100 comprises a system controller 110 connected to a software user interface 170 and a solenoid valve 140. The solenoid valve 140 is connected to a pressure regulator 130 which is connected in turn to an inert gas supply 120. Gas supply lines 150 connect the solenoid valve 140 to the reservoirs 21 and 31 as described below. A pressure sensor 160 is located in pump module 20b downstream of the pump and connected to the pump chip 23.

Referring to FIG. 9, the gas supply lines 150 are connected to the reservoirs 21 and 31 via channels 152 located in the pump module housing 22 and sensor module housing 32 respectively. The gas supply lines 150 pass through the base 50 and align with inlet port 154 on the lower surface of the pump module housing 22 and sensor module housing 32 respectively. Each gas supply interface is sealed by means of an o-ring 151. The channels 152 have an outlet port 153 which aligns with a space 155 formed by the outer portion 2 and the inner portion 3 of the reservoirs 21 and 31.

During the test, the system controller 110 applies gas pressure to the reagent reservoirs 21 and 31 by opening the solenoid valve 140 and letting the gas flow into the fluid circuit via gas supply lines 150. The system controller 110 then closes the solenoid valve 140 thus trapping a volume of pressurized gas in the circuit. Since the microfluidic circuit is closed, the pressure within the circuit should remain at a fixed level. If a fluidic module is missing or incorrectly sealed, the gas will leak out of the circuit and the pressure will rapidly drop to atmospheric pressure. The system controller 110 detects this drop in pressure and indicates the problem to the user via the software user interface 170.

Once the pressure test described above is complete, the system controller 110 will start a reaction by pumping reagents A and B, and solvent S, from each reagent reservoir 21 into the reaction chip 47. Typically one or more of the pump modules 20a, 20b, 20c will have an integrated pressure sensor 160 downstream of the pump to measure the fluid pressure. A rapid increase in pressure during pumping will indicate either a blockage in the reaction chip 47, misalignment between one or more of the fluid ports of the microfluidic modules or boiling of reagents in the reaction chip 47. A drop in pressure will indicate a fluid leak in the system or a pump failure. Positive pressure above the reagents in the reservoirs 21 can be used to aid the microfluidic pumping during operation of the apparatus.

Figure 10:
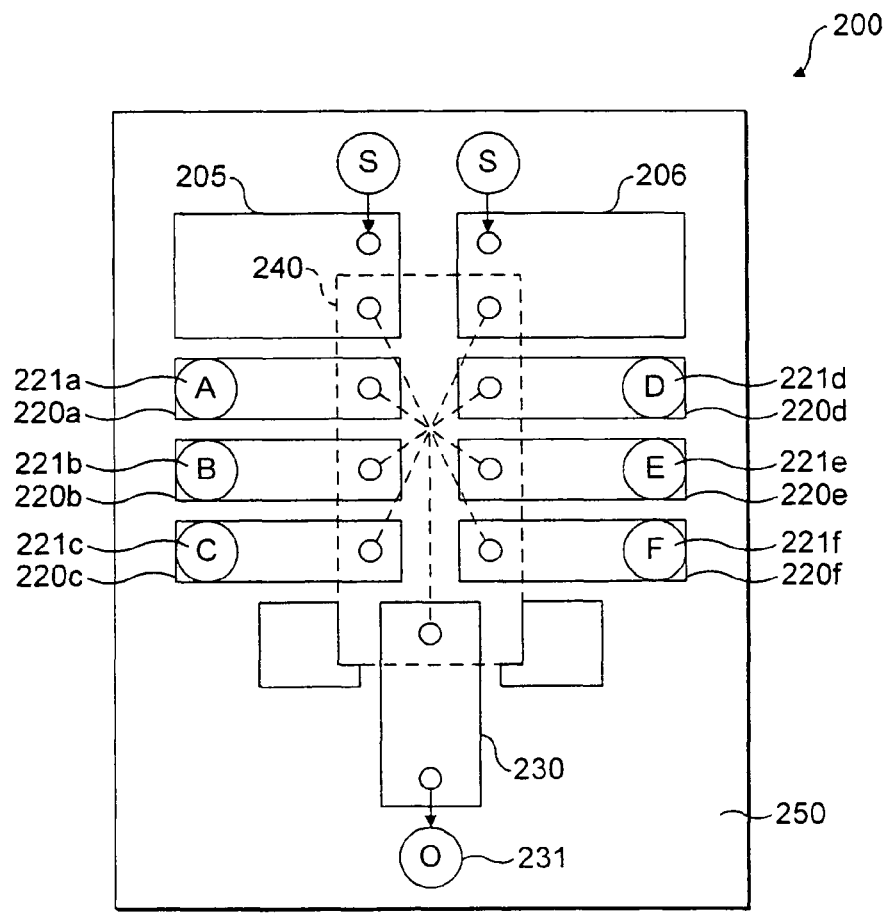
FIG. 10 is a schematic plan view of a further embodiment of the present invention.

A further example of a modular microfluidic apparatus 200 for mixing chemical reagents is shown in FIG. 10. In this example the apparatus 200 comprises a base 250 and a frame (not shown) moveably attached to the base in the same manner as described above. Six reagent input modules 220a-220f, an output module 230 and two pump modules 205, 206 are releasably attached to the base 250. A manifold module 240 is releasably attached to the frame. The apparatus 200 uses the same engagement method for the microfluidic modules as that described above Reagents A-F are stored in reservoirs 221a-221f. The reagent input modules 220a-220f contain valve chips that open to allow reagent to be drawn into the central manifold chip 240. The two pump modules 205, 206 draw the reagent into the manifold module 240, normally mixing the reagent with another reagent from another input module. The mixture is then dispensed by the pumps out through the output module 230 to an output reservoir 231.

The invention claimed is:

1. An apparatus for performing microfluidic processes comprising,
   a base,
   a plurality of fluidic modules releasably attached to the base, each fluidic module comprising a fluid port,
   a microfluidic manifold module comprising a plurality of ports,
   a frame attached to the base for releasably retaining the microfluidic manifold module, the frame being movable relatively to the base to move the microfluidic manifold module into contact with the fluidic modules such that each fluid port of the fluidic modules aligns and seals with a respective port on the microfluidic manifold module thus completing a microfluidic circuit.

2. An apparatus according to claim 1 wherein the ports of the microfluidic manifold module comprise a plurality of inlet ports and at least one outlet port.

3. An apparatus according to claim 1 wherein the frame comprises a sensor to detect the presence of the microfluidic manifold module.

4. An apparatus according to claim 1 wherein the frame is arranged to move linearly.

5. An apparatus according to any claim 1 wherein at least one of the fluidic modules is a non-microfluidic device.

6. An apparatus according to claim 1 wherein all of the fluidic modules are microfluidic devices.

7. An apparatus according to claim 1 wherein each fluidic module, and the microfluidic manifold module, have a housing surrounding an inner body to provide a support and location structure.

8. An apparatus according to claim 1 wherein each interface between a fluid port of the fluidic module and the corresponding port of the microfluidic manifold module is sealed by means of a resiliently deformable sealing member.

9. The apparatus of claim 8 wherein the sealing member is an o-ring.

10. The apparatus of claim 9 wherein the sealing member is an o-ring of generally annular shape with flat ends.

11. The apparatus of claim 8 wherein the sealing member is retained in a recess formed in the housing of a fluidic module.

12. The apparatus of claim 8 wherein the sealing member is retained in a recess formed in the housing of the microfluidic manifold module.

13. The apparatus of claim 1 wherein the frame is arranged to stop moving relatively to the base when a predetermined reaction force is reached.

14. The apparatus of claim 1 wherein the frame is arranged to stop moving relatively to the base when a predetermined position is reached.

* * * * *